United States Patent [19]

Elam

[11] 4,091,816

[45] May 30, 1978

[54] DOUBLE CUFFED ENDOTRACHEAL TUBE

[76] Inventor: James O. Elam, 6723 S. Euclid, Chicago, Ill. 60649

[21] Appl. No.: 763,354

[22] Filed: Jan. 28, 1977

[51] Int. Cl.$^2$ ............................................. A61M 25/00
[52] U.S. Cl. ................................ 128/351; 128/349 B; 128/208
[58] Field of Search ............ 128/348, 349 B, 349 BV, 128/350 R, 351, 325, 208

[56] References Cited

U.S. PATENT DOCUMENTS

| | | | |
|---|---|---|---|
| 2,849,001 | 8/1958 | Oddo | 128/349 B |
| 3,046,988 | 7/1962 | Moreau et al. | 128/349 B X |
| 3,638,655 | 2/1972 | Doherty | 128/351 |
| 3,931,822 | 1/1976 | Marici | 128/351 |

*Primary Examiner*—Dalton L. Truluck
*Attorney, Agent, or Firm*—Hosier, Niro & Daleiden, Ltd.

[57] ABSTRACT

A double cuff for endotracheal tubes is designed with two inflatable balloons, shaped to fully occupy the spaces above and below the open larynx. The two cuffs have a common inflation channel and therefore after their inflation are in free communication with each other. The lower cuff with its thin non-elastic walls rests in the upper trachea, applying a pressure against the walls of the upper trachea and subglottic structures determined by the behavior of an upper cuff whose walls are elastic. This elastic cuff occupies the space immediately above the larynx and extends slightly into the pharynx. Elastic properties of the upper cuff confer, in effect, a pressure relief system to the lower non-elastic cuff as a result of their interconnection through the common inflation channel. A short segment of uncuffed tube between the cuffs allows correct anatomical placement of this segment at the level of the larynx, insuring that the inelastic lower cuff rests below the larynx and the elastic upper cuff above the larynx. The proximity of the two cuffs results in an anchor effect around the glottic structures. Maintenance of a seal at low intracuff pressures in the trachea and larynx eliminates ciliary injury despite relatively high lung-inflating pressure because the latter is intermittently transmitted into the lower cuff which in turn is pressed against the subglottic structures to provide a satisfactory non-leaking seal for ventilation. Simultaneously the cuffs protect the larynx and trachea from aspiration of secretions from the upper airway into the lung and anchor the tube to prevent both bronchial intubation and inadvertent extubation.

8 Claims, 7 Drawing Figures

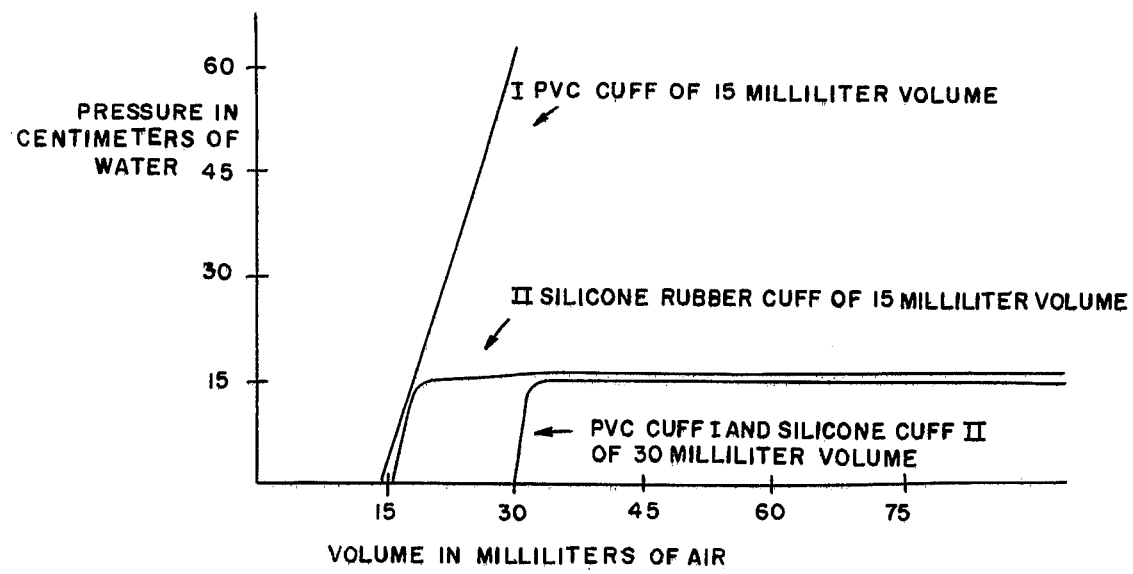

DOUBLE CUFFED ENDOTRACHEAL TUBE

BACKGROUND AND SUMMARY

This invention concerns a special design of double cuff placed near the distal tip of endotracheal tubes. Conventionally, a single cuff is inflated with air following insertion of the device into the human mid-trachea to achieve an airtight seal of the space between the tube and surrounding tracheal wall. As such the cuffed endotracheal tube has been routinely employed for many decades to prevent upper airway obstruction or to facilitate artificial ventilation of the unconscious or anesthetized patient. However, recent investigations have disclosed several defects in conventional cuffed endotracheal tubes. The double cuff herein described overcomes all of the following defects. These defects are, firstly, the failure to prevent secretions from accumulating in the upper trachea. Secondly, all tracheal tubes traverse the delicate structures of the larynx and abrade the vocal cords as a result of to and fro motion of the tube associated with respiration. Thirdly, the effects of intra-cuff sealing pressure upon the ciliated membranes lining the tracheal wall reversibly or permanently injure the cilia and surface membranes of the mid-trachea. The degree of injury is proportional to the magnitude of lateral-wall-cuff pressure in excess of 15 centimeters of water and to the duration such pressure is applied. Conventionally, the inflatable cuff is placed to rest in the mid-trachea several contimeters below the larynx, where compression of the ciliated endothelium of the trachea causes injury. Conventional endotracheal tube cuffs have a single cavity and produce a non-leak seal at pressures which occlude the blood perfusion of the tracheal mucosa and after a period of time produce tissue necrosis. By contrast the present invention consists of two cuffs in series which provide a total assembly which anchor the tube at points immediately above and below the larynx, thereby preventing bronchial intubation and inadvertent extubation.

One problem arising from prevailing practices of tracheal intubation is the failure of the conventional cuff to prevent secretions from passing through an unprotected space between the vocal cords and the endotracheal tube. The result is accumulation of a ring of contaminated material in the upper trachea above the inflated cuff which enters the lung when the cuff is deflated at extubation. During intubation this residue or ring of infected secretions trickles into the larynx and becomes entrapped above the inflated cuff until subsequent extubation allows the ring of secretions to enter the mid-trachea where injured cilia fail to protect the lung. The normal protective mechanisms by which the cilia carry the secretions upward in the respiratory tree until reflex coughing results in their removal fail to operate. My invention eliminates such aspiration by virtue of placing the upper inflatable cuff immediately above the larynx to keep the upper airway secretions from entering the laryngeal area. After insertion and initial inflation the cuff rests above the larynx thereby preventing exposure of the larynx and trachea to contamination. By leaving inflated the cuff described here, oral secretions may be removed by suction catheter with both the larynx and trachea protected. Thus, the present invention is superior to the conventional single cuffs in at least three important features, as herein embodied: (1) a positive means of anchoring the cuff between the cords, thereby preventing tube motion, accidental extubation, or further penetration of the cuffed tube into a bronchus, (2) low sealing pressure within the trachea and above the larynx and (3) secretions are excluded from the larynx or upper trachea.

The foregoing and other objects and advantages of the invention will be set forth in or are apparent from the following description and drawings:

DRAWINGS

In the Figures:

FIG. 7 is a graphic illustration of the pressure-volume relationships of two selected cuff materials and the resultant behavior of the double cuffed design of the invention.

DETAILED DESCRIPTION

Figure 1:
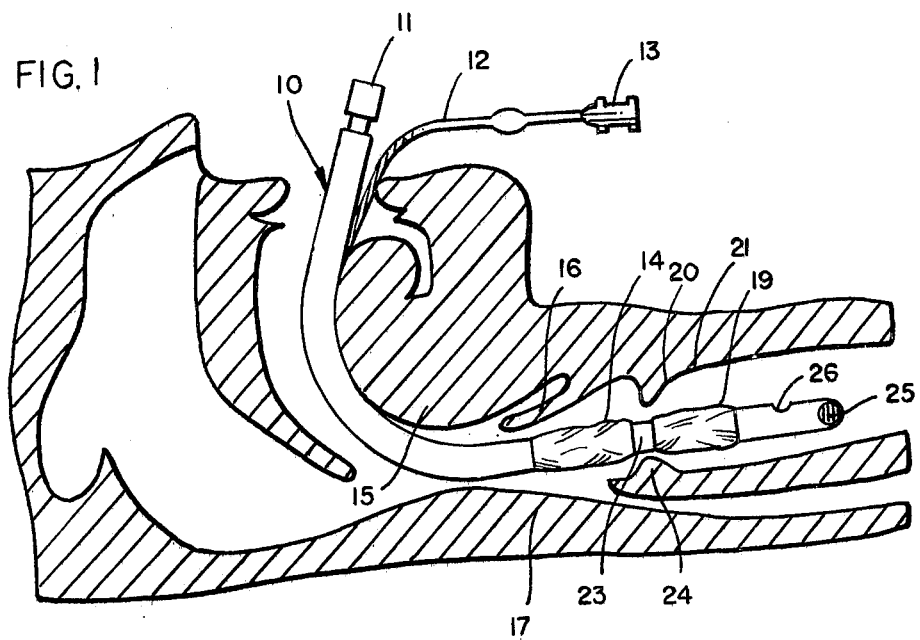
FIG. 1 is a partially cross-sectional partially schematic view of an embodiment of the invention installed in a patient, both cuffs deflated and resting above and below the larynx.
Figure 2:
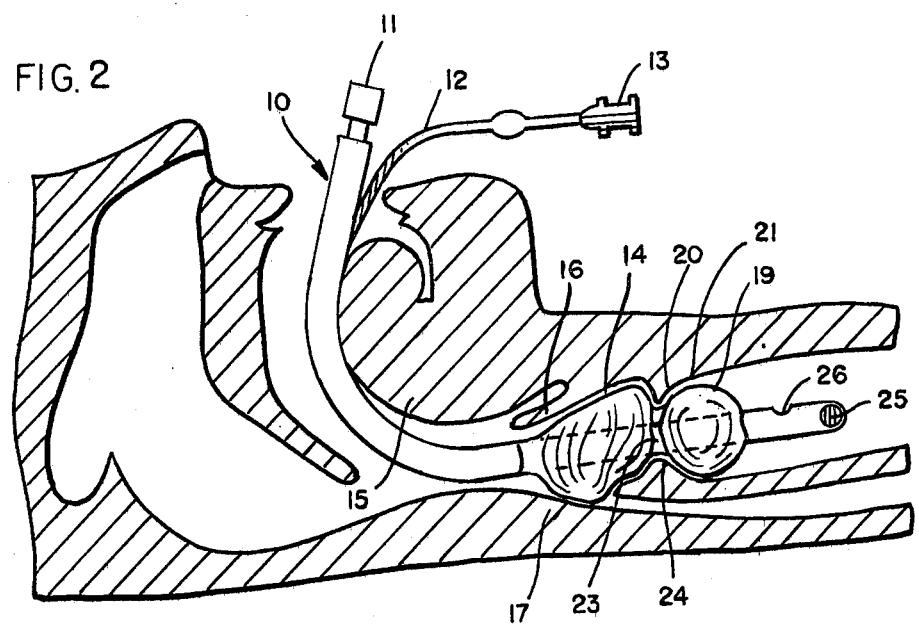
FIG. 2 is a view similar to FIG. 1 in which the cuffs are inflated above and below the larynx.
Figure 3:
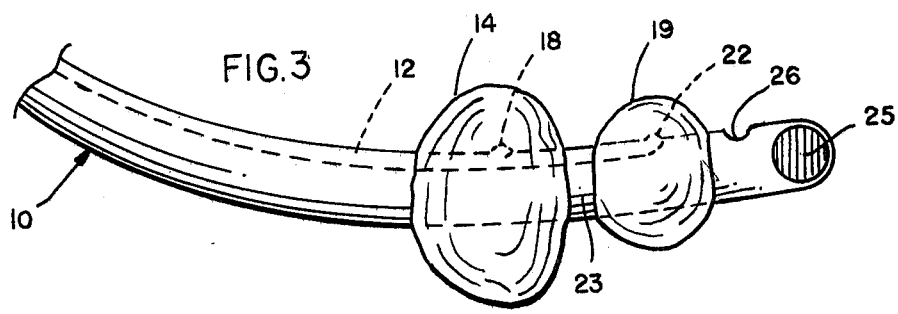
FIG. 3 is a cross-sectional view of the separate cuffs illustrating the small channel by which they are inflatable and deflatable and by which the two cuffs are in continuous intercommunication.

Referring to the FIG. 1, the head of a patient is shown in schematic cross-section with an endotracheal tube 10, its appropriate proximal connector 11, and an inflation-deflation channel 12, with an appropriate fitting 13, to attach a syringe. The upper cuff 14 of elastic material (silicone rubber) compresses the patient's tongue 15 and epiglottis 16 and posterior pharyngeal wall 17, being inflatable and deflatable via orifice 18 (FIG. 3) through channel 12. The lower cuff 19 has a non-elastic wall (polyvinylchloride) which impinges respectively against the patient's subglottis 20 and upper trachea 21 (FIG. 1), inflatable and deflatable via channel 12 through orifice 22 (FIG.3). The intercuff segment 23 of the tube lies within the larynx 24. The distal end of the tracheal tube 10 has a beveled opening 25 at its tip and a perforation 26 near its distal end. A pressure relief system, namely the elastic cuff 14, is in free communication continuously with the lower cuff 19.

Figure 4:
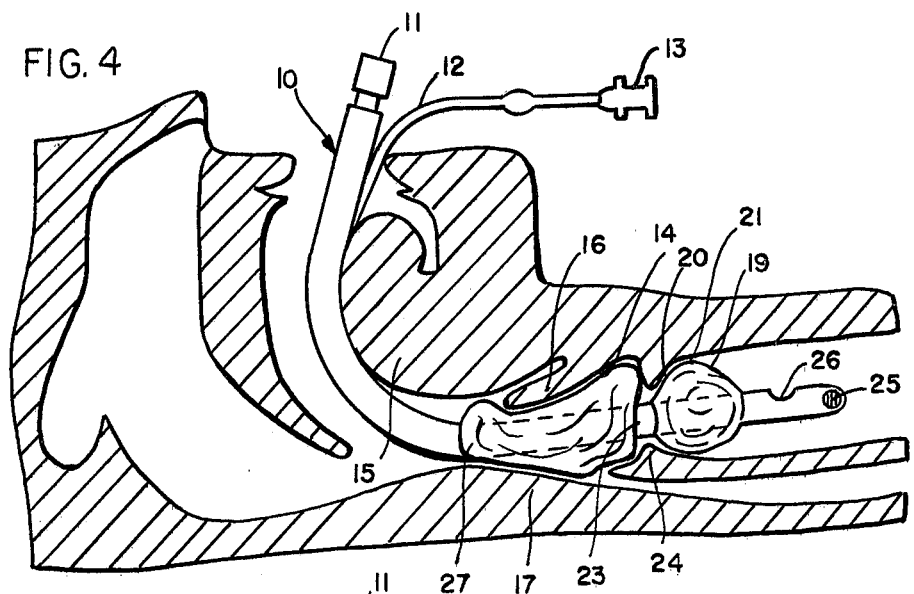
FIG. 4 is a view similar to FIG. 1 in depicting overinflation of the upper elastic cuff showing the lower non-elastic cuff normally inflated thereby maintaining low pressure in both the lower and upper cuffs.
Figure 5:
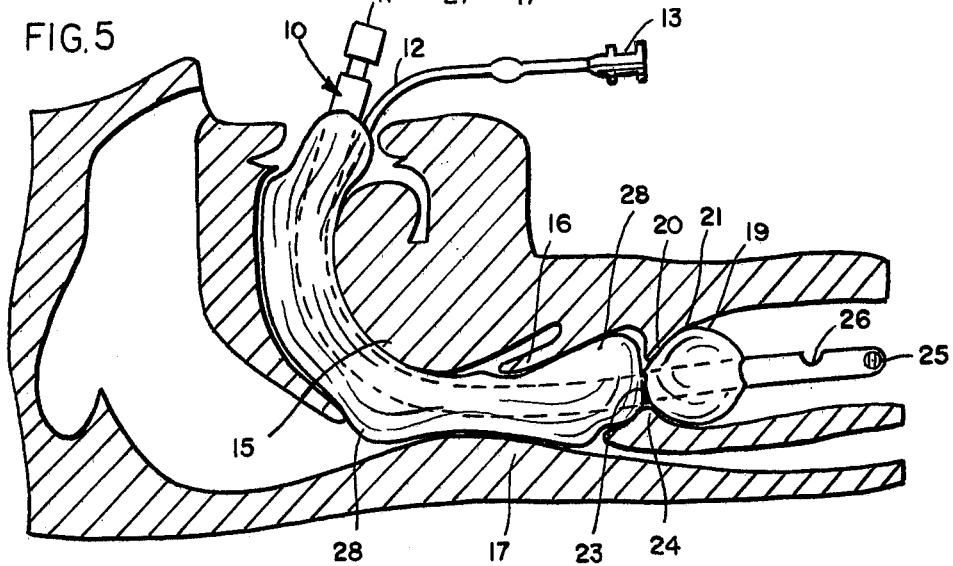
FIG. 5 is a view similar to FIG. 1 in which the upper elastic cuff has an elongated tubular configuration extending from the laryngeal area to the proximal end of the endotracheal tube.
Figure 6:
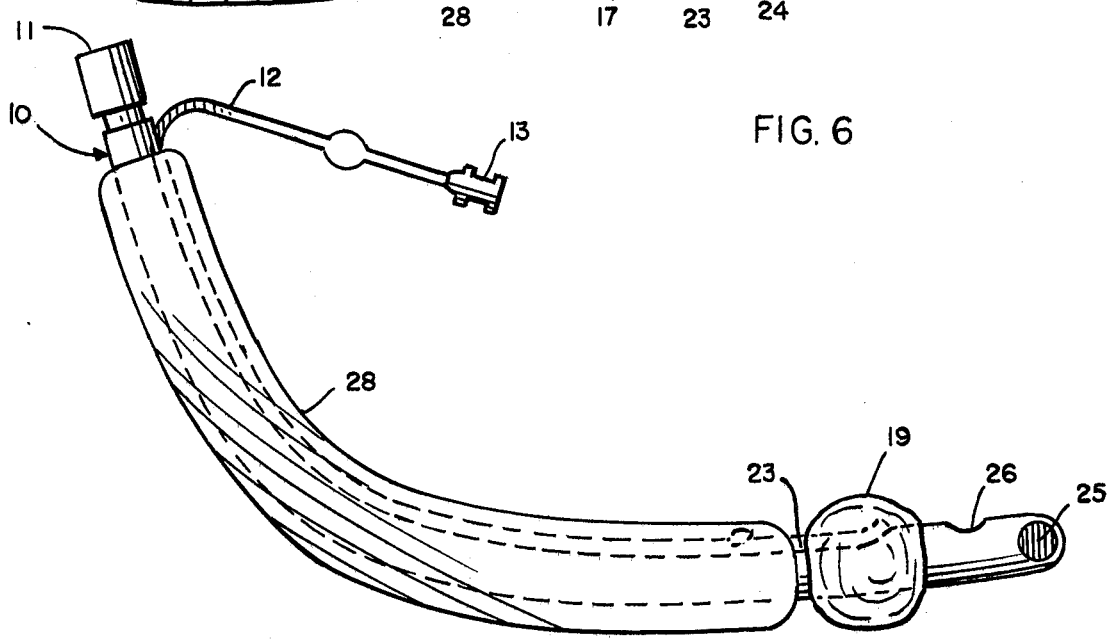
FIG. 6 is a cross-sectional view of the separate cuffs of FIG. 5 illustrating the small channel by which the cuffs are inflatable and noninflatable and by which the two cuffs are in continuous intercommunication.

The upper cuff allows overinflation 27 (FIG. 4) beyond its normally filled volume without elevation of intra-cuff pressures. Alternatively, the upper cuff may be extended as an elongated tubular shape 28 (FIGS. 5 & 6) to be secured near the proximal end of tube 10 thereby being visible and palpable in the patient's mouth for observing the state of inflation or collapse of the cuff system.

A conventional endotracheal tube has one channel integral in its wall to inflate and deflate a single cylindrical cuff. By contrast, this invention has two cuffs 14 and 19 in series inflatable and deflatable through a channel 12 which is integral with the wall of the tube 10, terminating within the lumena 18, 22, of two separate cuffs 14, 19. When both cuffs 14 and 19 are inflated they form together an overall appearance cuff with a dumbbell-like shape (FIG. 3). Although the two cuffs 14 and 19 are separated from one another by a segment 23 of the tube 10 they are simultaneously inflatable and deflatable through channel 12 and intercommunicate so that excessive amounts of air introduced by a syringe affect the volume of the upper elastic cuff 14 but not that of the lower cuff 19, such excessive volumes failing to elevate the intra-cuff pressures because of the elastic behavior of the upper cuff 14.

Thus, the design departs from the single cavity cuff. In contrast, a double cuff system 14, 19 with its single inflation means 12, is able to be inflated or deflated simultaneously. The two cuffs 14 and 19, may also be constructed contiguously without spacing apart, creating a notch to accommodate the larynx for a leak-tight pneumatic system.

Extubation without deflation does not injure the larynx because the air in the lower cuff 19 will be automatically transferred into the upper elastic cuff 14 and allow slippage through the larynx of the cuff 19 and distal tip of the tracheal tube 10.

Common inflation means 12, of the two cuffs 14 and 19 permits the use of a constant pressure at various inflation volumes. Thus, following insertion of the tube 10 into the trachea with both cuffs collapsed, the cuffs 14 and 19 are inflated to a pressure of say 14 centimeters of water by emptying a 30 milliliter syringe attached to fitting 13. If additional air is then inflated the intra-cuff pressures do not exceed 15 centimeters of water as only the upper elastic cuff expands. This level of pressure against the membrane lining the upper trachea will not interfere with the circulation of blood to these structures. The expanding upper cuff will impinge against the epiglottis 16, and pharyngeal wall 17, which are freely movable, and tolerate expansion of their adjacent spaces without injury. The lower cuff pressure of only 15 centimeters of water insures a well-tolerated lateral-wall pressure in the lower cuff without interference with perfusion of the tracheal mucosa. By virtue of the spacing of the cuffs the tube 10 is anchored by the cuffs 14, 19 to prevent accidental extubation. The pressure relief behavior of the upper cuff 14 allows considerable decompression of this part of the lower non-elastic cuff without permitting secretions to enter the trachea should the tube be forcibly withdrawn from the patient by erroneous technique prior to collapse of the cuff system.

Pharyngeal secretions are prevented from entering the larynx and trachea by the upper cuff 14. Such secretions may be removed from the pharynx by suction catheter prior to collapse of the upper cuff 14, thus preventing the secretions from being aspirated into the trachea at the time of extubation. Introduction of a suction catheter into the esophagus displaces the upper cuff 14 in order for the catheter tip to enter the esophagus. At such time, the maintained pressure in the upper cuff 14 protects the trachea and lungs from secretion contamination.

Further, since the cricoid and thyroid cartilages encircle the upper trachea, inflation of the cuffs 14, 19 to a pressure of 15 centimeters of water does not occlude the esophagus and thereby will not impede catheterization of the esophagus as do inflated conventional (midtracheal) cuffs. In the latter instance, the upper cuff 14 may be partially displaced to permit the catheter to pass into the esophagus or stomach, without decreasing the pressure in the lower cuff 19 during this otherwise vulnerable interval when secretions could be aspirated into the unprotected trachea. In other words, the double cuff of this invention eliminates hazards of the above procedures by providing safety incident to catheterization and suction of the pharynx, esophagus, and stomach.

The pressure-relief function of the upper cuff 14 also protects the lower cuff 19 from the pressure elevations which would otherwise occur if the patient elevates intrapulmonary pressure as in coughing or if nitrous oxide diffuses into the cuff through its walls. The pressure-volume relationships of the two selected cuff materials (as shown in FIG. 7) explain the aforementioned behavior of the double cuff design of this invention.

While in the foregoing specification a detailed description of the invention has been set forth for purposes of illustration, variation of the details herein given may be made by those skilled in the art without departing from the spirit and scope of the invention.

I claim:

1. An endotracheal airway device adapted for insertion through the mouth and into the trachea of a patient to provide a passage for artificial respiration comprising an elongated flexible air tube having proximal and distal end portions, an inflatable-deflatable pair of cuff means secured to and encircling said tube intermediate said proximal and distal end portions to define an upper cuff means and a lower cuff means, said upper and lower cuff means being adapted to accommodate the larynx and being in communication with one another, said upper cuff means having elastic properties, said lower cuff means being shaped to fit into the space defined by the upper trachea and subglottic regions, said lower cuff means having pliable inelastic properties, and means for inflating and deflating said upper and lower cuff means.

2. The device of claim 1 in which said inflation and deflation means consists of a single channel extending along said tube and having a proximal end portion for syringe attachment and having a distal end portion terminating within said upper and lower cuff means.

3. The device of claim 1 in which said upper cuff means distal end portion is contiguous with said proximal end portion of said lower cuff means.

4. The device of claim 1 in which said upper and lower cuff means have proximal and distal dimensions which after inflation cause said cuff means to fit into the spaces above and below the vocal chords thereby serving to anchor said tube against inadvertent movement into or out of the trachea.

5. The device of claim 1 in which said upper cuff means is having elastic properties serving thereby to limit and equalize pressure in said upper and lower cuff means as a result of said elastic properties of said upper cuff means and as a result of said upper and lower cuff means being in communication with one another.

6. The device of claim 5 in which said upper cuff means has an elongated tubular configuration extending along said tube from above said lower cuff means to said proximal end portion of said tube, thereby providing means in the patient of visuallizing and palpating the state of collapse or inflation of said upper cuff means.

7. The device of claim 5 in which said lower cuff means has a flat pressure behavior of approximately 15 centimeters of water with increasing volumes of air to insure lateral wall pressures which do not interfere with capillary perfusion of the membranes of the trachea and larynx.

8. The device of claim 5 in which said upper and lower cuff means provide safe withdrawal of said lower cuff means through the larynx in the state of inflation by causing the transfer of air from said lower cuff means automatically into said upper cuff means thereby allowing said lower cuff means to traverse the larynx in a collapsed fashion without applying an avulsive force to the vocal cords.

* * * * *

UNITED STATES PATENT AND TRADEMARK OFFICE
CERTIFICATE OF CORRECTION

PATENT NO. : 4,091,816

DATED : May 30, 1978

INVENTOR(S) : James O. Elam

It is certified that error appears in the above-identified patent and that said Letters Patent are hereby corrected as shown below:

Col. 1, line 30, change "contimeters" to --centimeters --.
Col. 4, line 54 after "is" insert -- shaped after inflation to fit snuggly into the space above the larynx, said upper and lower cuff means --.

Column 4, line 50, change "chords" to -- cords --.

Signed and Sealed this

Twenty-first Day of November 1978

[SEAL]

Attest:

RUTH C. MASON
Attesting Officer

DONALD W. BANNER
Commissioner of Patents and Trademarks